United States Patent
Huang et al.

(10) Patent No.: US 7,678,588 B2
(45) Date of Patent: Mar. 16, 2010

(54) METHOD FOR CONSTRUCTING MODULE FOR OPTICAL CRITICAL DIMENSION (OCD) AND MEASURING METHOD OF MODULE FOR OPTICAL CRITICAL DIMENSION USING THE MODULE

(75) Inventors: Chun-Chi Huang, Tainan County (TW); Wen-Yi Teng, Kaohsiung (TW)

(73) Assignee: United Microelectronics Corp., Hsin-Chu (TW)

( * ) Notice: Subject to any disclaimer, the term of this patent is extended or adjusted under 35 U.S.C. 154(b) by 138 days.

(21) Appl. No.: 12/017,596

(22) Filed: Jan. 22, 2008

(65) Prior Publication Data

US 2009/0186428 A1 Jul. 23, 2009

(51) Int. Cl.
*H01L 21/00* (2006.01)

(52) U.S. Cl. .............. 438/14; 438/15; 438/16; 438/17; 438/725; 438/736; 257/E21.053; 257/E21.256; 257/E21.312; 257/E21.314

(58) Field of Classification Search ............. 438/14–17, 438/714, 719, 725, 736; 257/E21.053, 256, 257/312, 314
See application file for complete search history.

(56) References Cited

U.S. PATENT DOCUMENTS

| | | | |
|---|---|---|---|
| 6,252,670 B1 * | 6/2001 | Sheng et al. ................. 356/504 |
| 6,258,610 B1 * | 7/2001 | Blatchford et al. ............ 438/14 |
| 6,326,618 B1 * | 12/2001 | Kane et al. .................. 250/307 |
| 6,420,702 B1 * | 7/2002 | Tripsas et al. ................ 250/310 |
| 6,623,994 B1 * | 9/2003 | Stirton ........................ 438/14 |
| 6,633,831 B2 * | 10/2003 | Nikoonahad et al. ........ 702/155 |
| 6,673,637 B2 * | 1/2004 | Wack et al. .................... 438/14 |
| 6,782,337 B2 * | 8/2004 | Wack et al. .................. 702/155 |
| 6,829,056 B1 * | 12/2004 | Barnes et al. ................ 356/625 |
| 6,982,176 B2 * | 1/2006 | Couture et al. ................ 438/14 |
| 7,094,613 B2 * | 8/2006 | Mui et al. ....................... 438/9 |
| 7,430,898 B1 * | 10/2008 | Weber-Grabau et al. ...... 73/105 |
| 7,498,106 B2 * | 3/2009 | Mui et al. ..................... 430/30 |
| 2004/0229471 A1 * | 11/2004 | Abdulhalim et al. ........ 438/736 |
| 2005/0157297 A1 * | 7/2005 | Abdulhalim et al. ........ 356/401 |
| 2005/0208685 A1 * | 9/2005 | Abdulhalim et al. .......... 438/14 |
| 2009/0186428 A1 * | 7/2009 | Huang et al. .................. 438/16 |

* cited by examiner

*Primary Examiner*—Michael S Lebentritt
(74) *Attorney, Agent, or Firm*—Winston Hsu

(57) ABSTRACT

An optical critical dimension measuring method, applicable in measuring a pattern, that includes a plurality of polysilicon layers, of a device, is provided. The method includes obtaining a real curve corresponding to the to-be-measured device. Then, determining whether an ion implantation process has been performed on the polysilicon layers, a different module is selected. A correlation process is performed according to the selected module to generate a theoretical curve that correlates with the real curve to obtain a plurality of parameters corresponding to the theoretical curve.

37 Claims, 6 Drawing Sheets

METHOD FOR CONSTRUCTING MODULE FOR OPTICAL CRITICAL DIMENSION (OCD) AND MEASURING METHOD OF MODULE FOR OPTICAL CRITICAL DIMENSION USING THE MODULE

BACKGROUND OF THE INVENTION

1. Field of Invention

The present invention relates to a method for measuring a to-be-measured device. More particularly, the present invention relates to a method of establishing an optical critical dimension module and a measuring method of using the optical critical dimension module.

2. Description of Related Art

Along with the development of semiconductor fabrication techniques, the level of integration of integrated circuits increases continuously and the critical dimensions correspondingly decrease. In order to achieve a high level of integration and high efficiency, the critical dimension of each characteristic feature, the profile and the degree of uniformity must be precisely controlled.

In the current semiconductor fabrication process, the characteristic feature is formed by a transferring of patterns via the photolithograph and etching techniques. A typical lithograph process includes a coating of a photoresist, a soft baking process, an exposure process, a development process and a hard baking process. The accuracy of a characteristic feature highly relates to the quality of the photoresist pattern. Hence, to ensure the quality of a photoresist pattern and to mitigate any process problems, an to ensure the quality of a photoresist pattern and to mitigate any process problems, an ADI (After Development Inspection) is normally performed subsequent to a development process. If after being inspected, the photoresist pattern is determined to contain defects, the photoresist needs to be removed and the fabrication process has to be re-conducted. If the photoresist pattern contains undetected defects, the etching performed in the subsequent etching process may be inaccurate, leading to irreparable errors and an ultimate disposal of the wafer.

The optical critical dimension measuring method, such as the spectrum critical dimension (SCD) measuring method, is applicable in the inspection of a photoresist pattern after a development process. According to the optical critical dimension method, the test key spectrum that corresponds to the photoresist pattern is being measured first to obtain the real curve. Thereafter, an appropriate module is obtained from a library, and a correlation process is performed to correlate the real curve of the spectrum with a theoretical curve. Based on the corresponding parameters of the theoretical curve, relevant information of the to-be-measured photoresist pattern is acquired.

Since a spectrum is obtained from an optical critical dimension method, the characteristics of each film layer underneath the photoresist pattern may influence the behavior of the spectrum curve. Hence, during the construction of the modules of the library, the corresponding film file of each film layer that is underneath the photoresist pattern is obtained to establish a corresponding stacked film.

In the fabrication of a gate, the photoresist pattern covers the polysilicon layer and the gate oxide layer. Accordingly, when the optical critical dimension measuring method is used to measure a photoresist pattern, a module that includes a polysilicon and silicon oxide stacked layer is selected from the library to perform the correlation. Further, during the correlation, the thickness and the optical parameters, such as refraction index or extinction coefficient of each material layer are defined at certain fixed values. However, with the current approach, the theoretical curve and the real curve of the spectrum are unable to correlate. The corresponding parameters of the theoretical curve do not accurately reflect the actual conditions of the photoresist pattern. Hence, factual information regarding the photoresist pattern is unable to obtain.

SUMMARY OF THE INVENTION

The present invention is to provide an optical critical dimension measuring method, wherein the to-be-measured pattern of a device can be accurately measured to obtain better relevant information of the to-be-measured pattern.

The present invention is to provide a method of constructing an optical critical dimension module, wherein the constructed module conforms closely to the actual conditions of the to-be-measured device. Hence, the theoretical curve correlates well with the real curve.

The present invention provides a spectrum critical dimension measuring method, wherein the method is applicable in detecting a to-be-measured pattern of a device, wherein the to-be-measured pattern includes a plurality of polysilicon layers there-under. The method includes obtaining a corresponding real curve of a to-be-measured device. Then, different modules are selected depending on whether an ion implantation has been performed on the polysilicon layers. When no ion implantation has been performed on the polysilicon layers, a first module is selected, wherein the first module is constructed with a first stacked layer. The first stacked layer includes a polysilicon material layer, but does not include an amorphous silicon material layer. When the polysilicon layer has been subjected to an ion implantation process and the surface of the polysilicon layer has been formed with an amorphous silicon layer, a module is selected depending on whether a thermal process has been performed to sufficiently crystallize the amorphous layer. When the polysilicon layer has not been subjected to a thermal process or the amorphous layer has not been completely crystallized to a polysilicon layer, a second module is selected. The second module is constructed with a second stacked layer. The second stacked layer includes a polysilicon material layer and an amorphous silicon material layer above the polysilicon layer. When the polysilicon layer has already been subjected to a thermal process, and when the amorphous layer is completely crystallized into the polysilicion layer, a third module is selected. The third module is constructed with a third stacked layer. The third stacked layer includes a polysilicon material layer, but does not include an amorphous silicon material layer. Thereafter, a correlation process is performed with the selected module to generate a theoretical curve that actually correlates with the real curve, and a plurality of parameters corresponding to the theoretical curve is obtained.

According to the embodiments of the invention, in the above-mentioned optical critical dimension measuring method, when the second module is selected, the thickness of the polysilicon material layer and the optical parameters of the polysilicon material layer and the amorphous silicon material layer are defined at a fixed value, while the thickness of the amorphous silicon layer is set at floating during the correlation process.

According to the embodiments of the invention, in the above-mentioned optical critical dimension measuring method, the amorphous material layer in the second stacked layer is a single layer, a double layer or a multi layer.

According to the embodiments of the invention, in the above-mentioned optical critical dimension measuring method, the ion implantation process is a doping process, and the polysilicon layer in the first stacked layer includes an undoped polysilicon material layer, the polysilicon layer in the second stacked layer includes a doped polysilicon material layer, and the polysilicon layer in the third stacked layer includes doped polysilicon material layer.

According to the embodiments of the invention, in the above-mentioned optical critical dimension measuring method, the doping process includes an N-type dopant implantation process or a P-type dopant implantation process.

According to the embodiments of the invention, in the above-mentioned optical critical dimension measuring method, when the to-be-measured pattern includes a photoresist pattern, and the polysilicon layer further includes a bottom layer, the first stacked structure includes, from bottom to top, a bottom material layer, a polysilicon material layer and a photoresist material layer; the second stacked structure includes, from bottom to top, a bottom material layer, a polysilicon material layer, an amorphous material layer and a photoresist material layer.

According to the embodiments of the invention, in the above-mentioned optical critical dimension measuring method, when the to-be-measured pattern is a photoresist pattern, and the polysilicon layer and the to-be-measured pattern further includes a mid layer therebetween, the first stacked structure includes, from bottom to top, a polysilicon material layer, a mid-material layer and a photoresist material layer, while the second stacked structure includes, from bottom to top, a polysilicon material layer, an amorphous silicon material layer, a mid-material layer and a photoresist material layer.

According to the embodiments of the invention, in the above-mentioned optical critical dimension measuring method, the thermal process includes a direct anneal process and an indirect anneal process.

According to the embodiments of the invention, the above-mentioned optical critical dimension measuring method includes normal incidence (NI) optical critical dimension measuring method or a spectroscopic ellipsometry (SE) optical critical dimension (SE-OCD) measuring method, wherein the spectroscopic ellipsometry optical critical dimension measuring method includes spectrum critical dimension measuring method.

The present invention provides a method of establishing an optical critical dimension module, wherein the optical critical dimension module is applicable in measuring a to-be-measured pattern that includes a pre-layer underneath. The method includes constructing a plurality of modules in accordance to the to-be-measured pattern, the type of each layer underneath the to-be-measured pattern and the various processes that have been performed on each layer. These modules include a first module and a second module. The first module is applicable to the pre-layer of the to-be-measured device prior a treatment process. The first module is established with a first stacked layer, and the first stacked layer includes, from bottom to top, a pre-material layer and a to-be-measured material layer, but does not include the treatment layer. The second module is applicable to a pre-layer of a to-be-measured layer after undergoing a treatment process to become a treatment layer. The second module is established with a second stacked layer, and the second stacked layer includes a pre-material layer, a treatment material layer and a to-be-measured material layer.

According to the embodiments of the invention, in the above-mentioned optical critical dimension measuring method, the treatment material in the second stacked layer is a single layer, a double layer or a multi layer.

According to the embodiments of the invention, in the above-mentioned optical critical dimension measuring method, the pre-layer includes a polysilicon layer and the pre-material layer includes a polysilicon material layer.

The treatment process includes a dopant implantation process, an oxidation process or a nitridation process; the treatment layer includes a doped amorphous silicon layer, an oxide layer or a nitride layer; the treatment material layer includes a doped amorphous silicon material layer, an oxide material layer or a nitride material layer.

According to the embodiments of the invention, in the above-mentioned optical critical dimension measuring method, these modules further include a third module. The third module is constructed with a third stacked layer. The third stacked layer includes, from bottom to top, a doped polysilicon material layer and a to-be-measured material layer. Further, the doped polysilicon material layer and the to-be-measured material layer do not include a doped amorphous silicon layer therebetween, and the third stacked layer is applicable to a to-be-measured device in which a thermal process is further performed after a dopant implantation process as a treatment process for the doped amorphous silicon layer to crystallized into a doped polysilicon layer.

According to the embodiments of the invention, in the above-mentioned optical critical dimension measuring method, the pre-layer includes a metal layer, the pre-material layer includes a metal material layer, the treatment layer includes a metal-silicon alloy layer; the treatment material layer includes a metal alloy material layer.

According to the embodiments of the invention, in the above-mentioned optical critical dimension measuring method, as the pre-layer and the to-be-measured pattern further includes a mid layer there-between; the first stacked layer further includes a mid-material layer positioned between the pre-material layer and the to-be-measured material layer; the second stacked layer further includes a mid-material layer configured between the treatment material layer and the to-be-measured material layer.

According to the embodiments of the invention, in the above-mentioned optical critical dimension measuring method, when the pre-layer is configured underneath the to-be-measured pattern, the pre-material layer of the first stacked layer is configured directly underneath the to-be-measured material layer, while the treatment material layer of the second stacked layer is configured directly underneath the to-be-measured material layer.

According to the embodiments of the invention, in the above-mentioned optical critical dimension measuring method, the pre-layer further includes a bottom layer underneath; the first stacked layer further includes a bottom material layer positioned under the pre-material layer; the second stacked layer further includes a bottom material layer under the pre-material layer.

According to the embodiments of the invention, the above-mentioned optical critical dimension measuring method includes a normal incident (NI) optical critical dimension measuring method or a spectroscopic ellipsometry (SE) optical critical dimension (SE-OCD) measuring method, wherein the spectroscopic ellipsometry optical critical dimension measuring method includes spectrum critical dimension measuring method.

The present invention provides an optical critical dimension measuring method, applicable in detecting a first to-be-measured pattern and a second to-be-measured pattern of a to-be-measured device. The first to-be-measured pattern further includes an undoped polysilicon layer thereunder, the second to-be-measured pattern further includes a doped polysilicon layer thereunder, and a portion of the doped polysilicon layer is amorphorized into a doped polysilicon layer. This method includes a first real curve corresponding to a first to-be-measured pattern and a second real curve corresponding to a second to-be-measured pattern. Thereafter, selecting a first module and a second module, in which the first module and the second module are different and are respectively used to perform correlation processes on the first real curve and the second real curve to obtain a plurality of first parameters corresponding to the first theoretical curve and a plurality of second parameters corresponding to the second theoretical curve.

According to an embodiment of the present invention, in the above method of establishing an optical critical dimension module, the first module is established with a first stacked layer, wherein the first stacked layer includes an undoped polysilicon material layer, but does not include an amorphous silicon layer. The second module is established with a second stacked layer. The second stacked layer includes a doped polysilicon material layer and a doped amorphous silicon material layer positioned above the doped polysilicon material layer.

According to an embodiment of the present invention, in the above method of establishing an optical critical dimension module, when the second module is selected to correlate with the second real curve, the optical parameters of the doped polysilicon material layer and the doped amorphous silicon material layer and the thickness of the doped silicon material layer are defined at a fixed value, while the thickness of the doped amorphous material layer is set at floating.

According to an embodiment of the present invention, the above method of establishing an optical critical dimension module includes a normal incident (NI) optical critical dimension measuring method or a spectroscopic ellipsometry (SE) optical critical dimension (SE-OCD) measuring method, wherein the spectroscopic ellipsometry optical critical dimension measuring method includes spectrum critical dimension measuring method.

According to the embodiments of the present invention, in the above method of constructing an optical critical dimension module, more accurate information of the to-be-measured pattern are obtained.

According to the embodiments of the present invention, in the above method of constructing an optical critical dimension module, the theoretical curve closely correlate with the real curve of the spectrum.

In order to make the aforementioned and other objects, features and advantages of the present invention comprehensible, a preferred embodiment accompanied with figures is described in detail below.

DESCRIPTION OF EMBODIMENTS

The characteristics of each film layer underneath the to-be-measured pattern would influence the curve behavior of the spectrum obtained from optical critical dimension detection. Accordingly, as the stacked layer of each module is being established in the library in the present invention, not only the type of each film layer is considered, the effects of a surface treatment process or other processes incurred on each film layer prior to the performance of the optical critical dimension measurement are also being considered. Hence, in accordance to the optical critical dimension measuring method of the invention, relevant information regarding the to-be-measured pattern of a device is obtained by selecting an appropriate module from the library to perform the correlation process. The optical critical dimension measuring method includes, for example, normal incident (NI) optical critical dimension measuring method or spectroscopic ellipsometry (SE) optical critical dimension (SE-OCD) measuring method, wherein the SE-OCD method includes, for example, the spectrum critical dimension (SCD) measuring method. The present invention now will be described more fully hereinafter with reference to optical critical dimension. However, it is to be understood that these embodiments are presented by way of example and not by way of limitation. The intent of the following detailed description is to cover all optical critical measuring methods as may fall within the spirit and scope of the invention as defined by the appended claims.

Figure 1A:
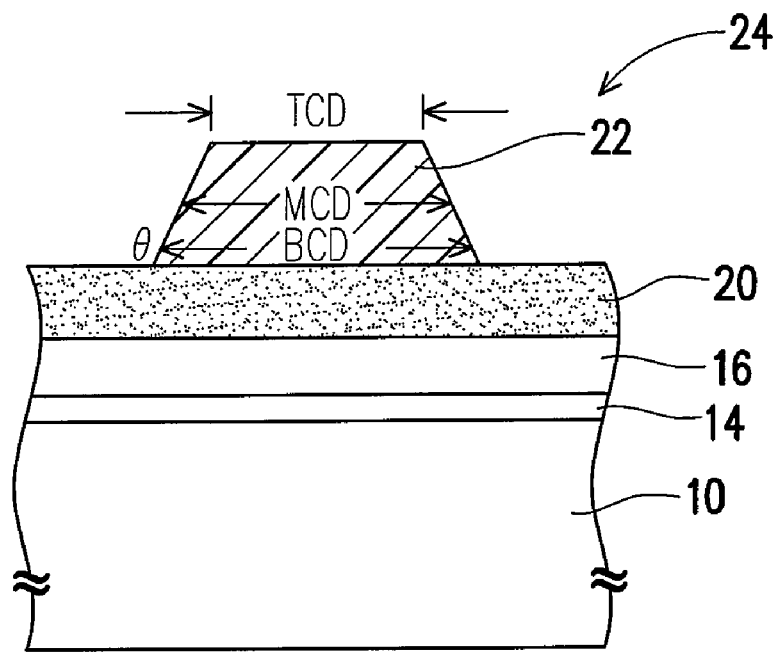
FIGS. 1A and 1D are schematic, cross-sectional view of a to-be-measured device according to an embodiment of the invention.
Figure 1B:
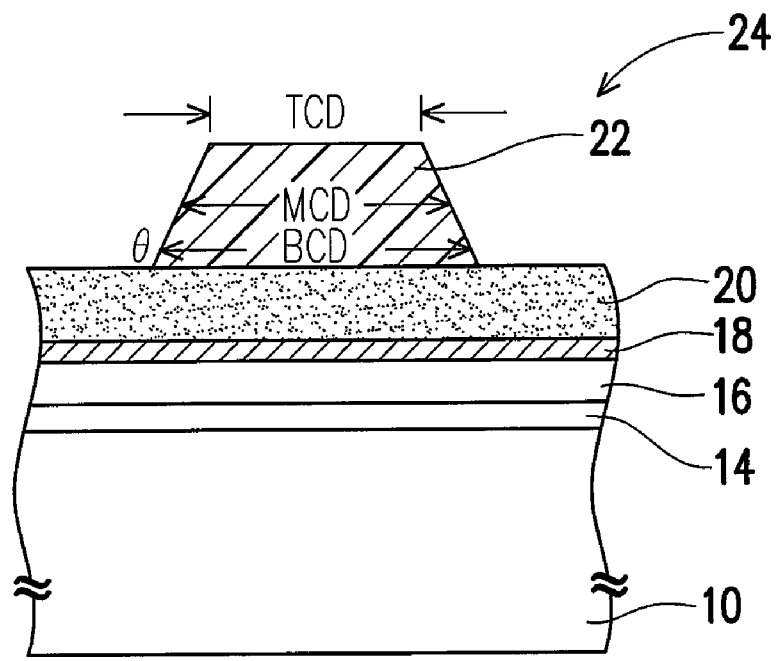

FIGS. 1A and 1B are schematic, cross-sectional view of a to-be-measured device.

Figure 1C:
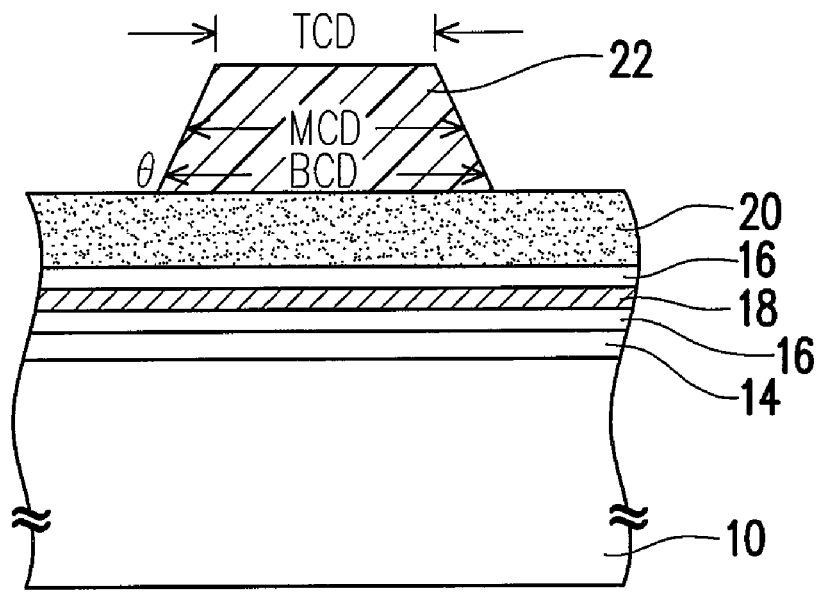
Figure 1D:
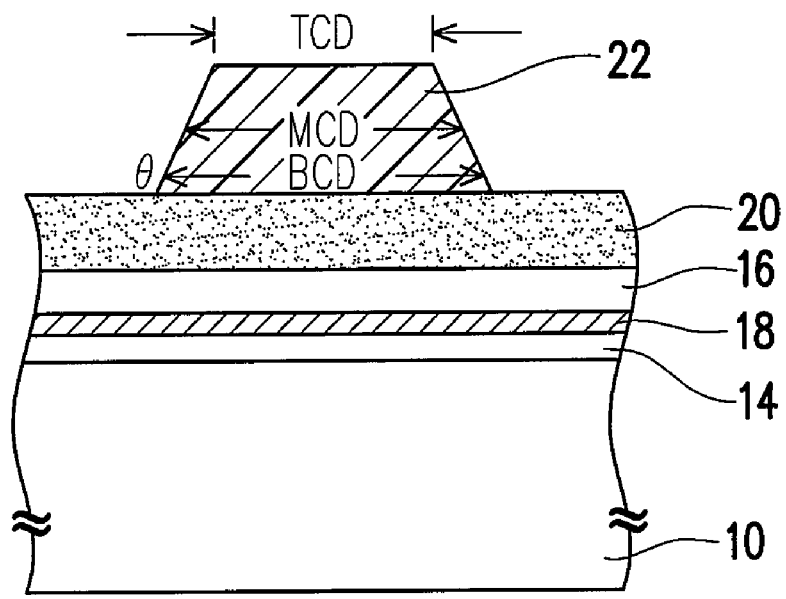

Referring to FIGS. 1A and 1B, the to-be-measured device is, for example, a wafer 10 including a to-be-measured pattern 22 and a pre-layer 16. The to-be-measured pattern 22 is, for example, a patterned photoresist layer. The pre-layer 16 can be a single layer, for example, a polysilicon layer, a copper layer, or other type of layer. The pre-layer 16 can also be a double layer or a multi layer. If prior to the SCD detection, the pre-layer 16 has not been pre-treated, the pre-layer 16 remains unchanged and the structure of the to-be-measured layer 24 is as shown in FIG. 1A. If prior to the performance of SCD detection, for example, before or after forming the to-be-measured pattern 22, a treatment layer 18 is formed on the surface of the pre-layer 16 by a surface treatment process, the structure of the to-be-measured device 24 is as shown in FIG. 1B. The surface treatment includes an ion implantation process, a nitridation process, an oxidation process or an alloying process. However, the treatment being performed prior to the SCD measuring on the pre-layer 16 is not limited to surface treatment, it may include the treatment on a mid-section of the pre-layer 16 to provide the treatment layer 18 at the mid-section of the pre-layer as shown in FIG. 1C. Additionally, as shown in FIG. 1D, the treatment may be directed to the bottom of the pre-layer 16 to provide a treatment layer 18 at the bottom of the pre-layer 16.

In one embodiment, the to-be-measured device 24 includes not only the wafer 10 having the to-be-measured pattern 22 and the pre-layer 16, it may include a mid-layer 20 between the pre-layer 16 and the to-be-measured pattern 22. The mid-layer 20 is, for example, a hard mask layer. In another embodiment, the to-be-measured device 24 includes not only the wafer 10 having the to-be-measured pattern 22 and a pre-layer 16, it further includes a bottom layer 14 between the to-be-measured pattern 22 and the wafer 10. The bottom layer 14 is, for example, a gate dielectric layer, and the material of the gate dielectric layer includes but not limited to silicon oxide or other high dielectric constant material.

Simply for the purpose of illustration, the following disclosure describes a surface treatment as the treatment process being performed on the pre-layer of a to-be-measured device.

Figure 2:
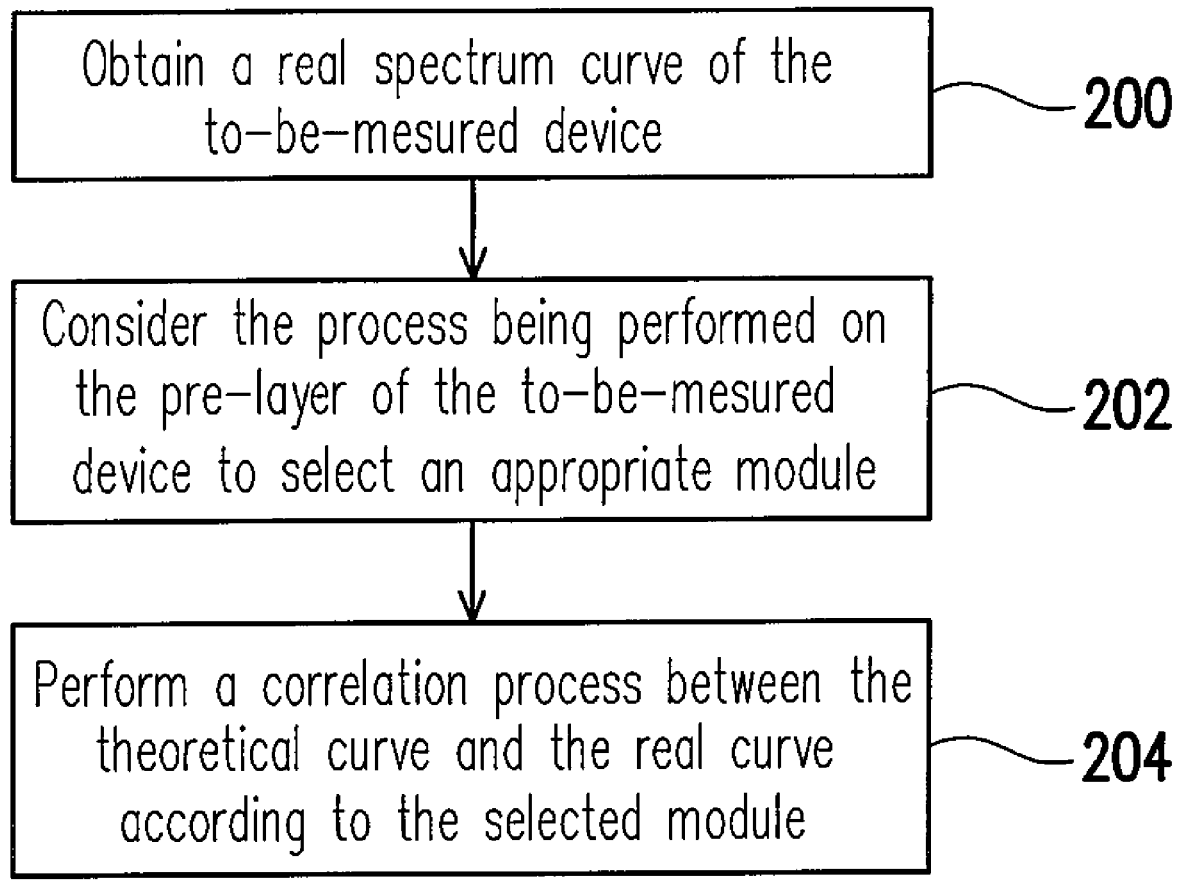
FIG. 2 is a flow chart of steps in exemplary processes that may be used in a method of measuring optical critical dimension according to an embodiment of the present invention.

FIG. 2 is a flow chart of steps in exemplary processes that may be used in a method of measuring optical critical dimension according to an embodiment of the present invention.

Referring to FIG. 2, the optical critical dimension measuring method of the embodiment of the present invention includes performing step 200, in which a spectrum of a to-be-measured device 10 is acquired to obtain the real curve. Thereafter, in step 202, an appropriate module is selected from the library. In selecting the appropriate module, not only the type of each layer in the to-be-measured device is considered, whether the pre-layer 106 in the to-be-measured device has been subjected to a surface treatment in forming a treatment layer 108 is also being considered. Further, asides from considering whether the pre-layer 106 in the to-be-measured device has been subjected to a surface treatment process, the subsequent process being performed on the surface treatment layer 108 following the surface treatment process, which may induce changes or dematerize the surface treatment layer 108 is also being considered.

In general, in selecting the appropriate module, a plurality of modules is already constructed in the library. In the present invention, these modules are established with stacked layers in film files, wherein each stacked layer is established according to the type of each layer of the to-be-measured device and the various effects being induced on the film layer by the various processes. In one embodiment, the library includes multiple types of modules, respectively illustrated in FIGS. 3, 4, 5 and 6.

Figure 3:
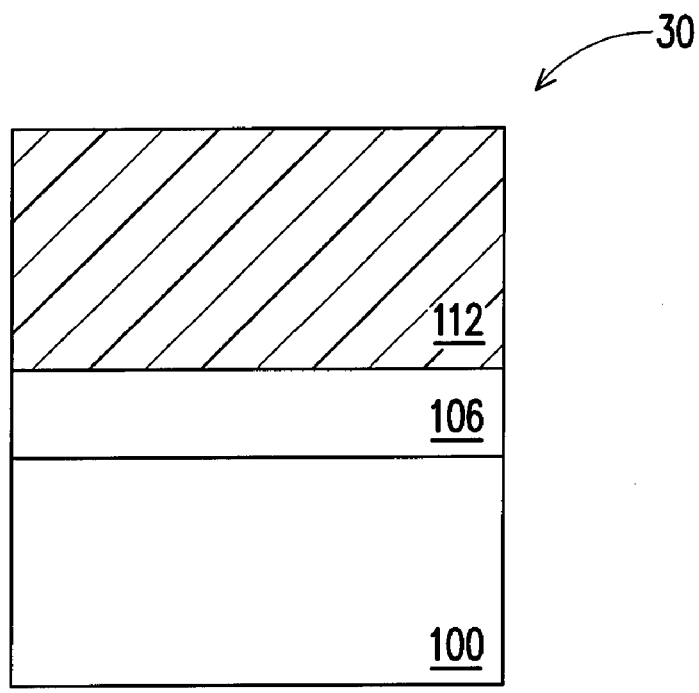
FIGS. 3, 4, 5, 6 are respectively schematic, cross-sectional views of the stacked layer of each module for constructing the library.

Referring to FIG. 3, the library includes a module established with the stacked layer 30. The stacked layer 30 includes, from top to bottom, a to-be-measured material layer 112, a pre-material layer 106 and a wafer material layer 100. The to-be-measured material layer 112 is, for example, a photoresist layer. The pre-material layer 106 is, for example, a polysilicon material layer, a copper material or other material layer. If the to-be-measured device 24 includes the wafer 10 having only the to-be-measured pattern 22 and the pre-layer 16, and prior to the SCD detection, the pre-layer 16 has not been subjected to a surface treatment, the module established with the stacked layer 30 may be selected. The values of the optical parameters of the to-be-measured material layer 112, the pre-material layer 106, and the wafer material layer 100 are respectively similar to those of the to-be-measured pattern 22, the pre-layer 16 and the wafer 10 of the to-be-measured device 24.

Figure 4:
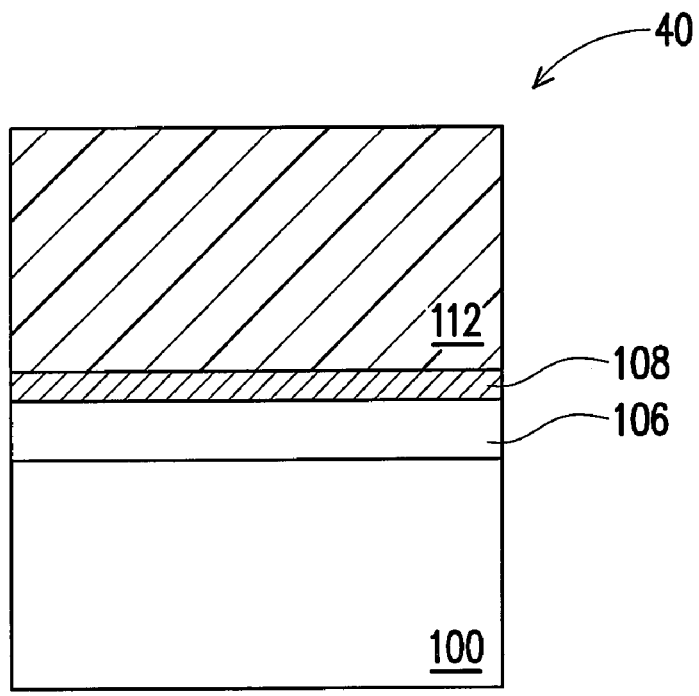

Referring to FIG. 4, the library includes the module established with the stacked layer 40. The stacked layer 40 includes, form top to bottom, a to-be-measured material layer 112, a treatment material layer 108, a pre-material layer 106 and a wafer material layer 100. The to-be-measured material layer 112 is, for example, a photoresist layer. The pre-material layer 112 is, for example, a polysilicon material layer, a copper material layer or other material layer.

If the to-be-measured device 24 includes the wafer 10 having only to-be-measured pattern 22 and the pre-layer 16, and prior to the SCD detection, for example, before or after forming the to-be-measured material layer 12, the pre-layer 16 has been subjected to a surface treatment, for example, an ion implantation process to form a treatment layer 18 on the surface of the pre-layer 16, the module established with the stacked layer 40 may be selected. The values of the optical parameters of the to-be-measured material layer 112, the treatment material layer 108, the pre-material layer 106, and the wafer material layer 100 are respectively similar to those of the to-be-measured pattern 22, the treatment layer 108, the pre-layer 16 and the wafer 10 of the to-be-measured device 24.

If the to-be-measured device 24 includes the wafer 10 comprising only the to-be-measured pattern 22 and the pre-layer 16, and prior to the SCD detection, for example, before or after forming the to-be-measured material layer 12, the pre-layer 16 has been subjected to a surface treatment, for example, an ion implantation process to form a treatment layer 18 on the surface of the pre-layer 16, and a subsequent process, such as a thermal process is performed to restore the treatment layer 18 back to the pre-layer 16 or a film similar to the pre-layer 16, the module established with the stacked layer 30 as shown in FIG. 3 and not the module established with the stacked layer 40 as shown in FIG. 4 is selected. The materials of the to-be-measured material layer 112, the pre-material layer 106, and the wafer material layer 100 in the stacked layer 30 are respectively similar to those of the to-be-measured pattern 22, the surface-treated and the subsequent-process-treated pre-layer 16 and the wafer 10 of the to-be-measured device 24.

Referring to FIG. 5A, the library includes the modules established with the stacked layer 50. The stacked layer 50 includes, from top to bottom, a to-be-measured material layer 112, a pre-material layer 106, and a wafer material layer 100, and optionally includes a mid-material layer 110 and a bottom material layer 104. The to-be-measured material layer 112 includes, for example, a photoresist layer. The mid-material layer 110, for example, a hard mask layer, is configured between the to-be-measured material layer 112 and the pre-material layer 106. The pre-material layer 106 includes for example, a polysilicon layer, a copper material layer, or other material layer. The bottom material layer 104, configured between the pre-material layer 106 and the wafer material layer 100, includes, for example, a dielectric layer, and a material of the dielectric layer includes silicon oxide or other high dielectric constant material layers, for example. If the to-be-measured device 24 includes the wafer 10 comprising only the to-be-measured pattern 22, the mid-layer 20, the pre-layer 16 and the bottom layer 14, and prior to performing the detection, the pre-layer 16 has not been surface-treated, the module established with the stacked layer 50 may be selected. The materials of the to-be-measured material layer 112, the mid-material layer 110, the pre-material layer 106, the bottom material layer 104 and the wafer material layer 100 in the stacked layer 50 are respectively similar to those of the to-be-measured pattern 22, the mid-layer 18, the pre-layer 16, the bottom layer 14 and the wafer 10 of the to-be-measured device 24.

Figure 6:
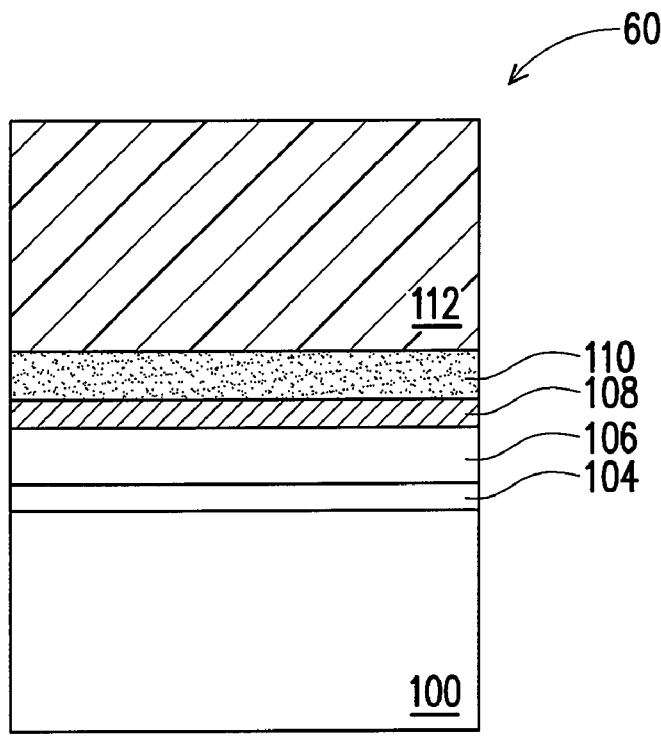

Referring to FIG. 6, the library includes the module constructed with the stacked layer 60. The stacked layer 60 includes, from top to bottom, the to-be-measured material layer 112, the treatment material layer 108, the pre-material layer 106 and the wafer material layer 100, and optionally includes a mid-material layer 110 and a bottom material layer 104. The to-be-measured material layer 112 includes, for example, a photoresist layer. The mid-material layer 110, for example, a hard mask layer, is configured between the to-be-measured material layer 112 and the pre-material layer 106. The pre-material layer 112 includes, for example, a polysilicon material layer, a copper material layer or other material layer. The bottom material layer 104, positioned between the pre-material layer 106 and the wafer material layer 100, includes, for example, a dielectric layer, and a material of the dielectric layer includes but not limited to silicon oxide or other high dielectric constant material layer.

If the to-be-measured device 24 includes the wafer 10 having only the to-be-measured pattern 22, the mid-layer 20, the pre-layer 16 and the bottom layer 14, and prior to performing the detection, for example, before or after the formation of the to-be-measured material layer 12, the pre-layer 16 has been surface-treated, for example, by an ion implantation process, to form a treatment layer 18 on the surface of the pre-layer 16, the module established with the stacked layer 60 may be selected. The values of the optical parameters of the to-be-measured material layer 112, the mid-material layer 110, the treatment layer 108, the pre-material layer 106, the bottom material layer 104 and the wafer material layer 100 in the stacked layer 60 are respectively similar to those of the to-be-measured pattern 22, the mid-layer 20, the treatment layer 108, the pre-layer 16, the bottom layer 14 and the wafer 10 of the to-be-measured device 24.

Figure 5:
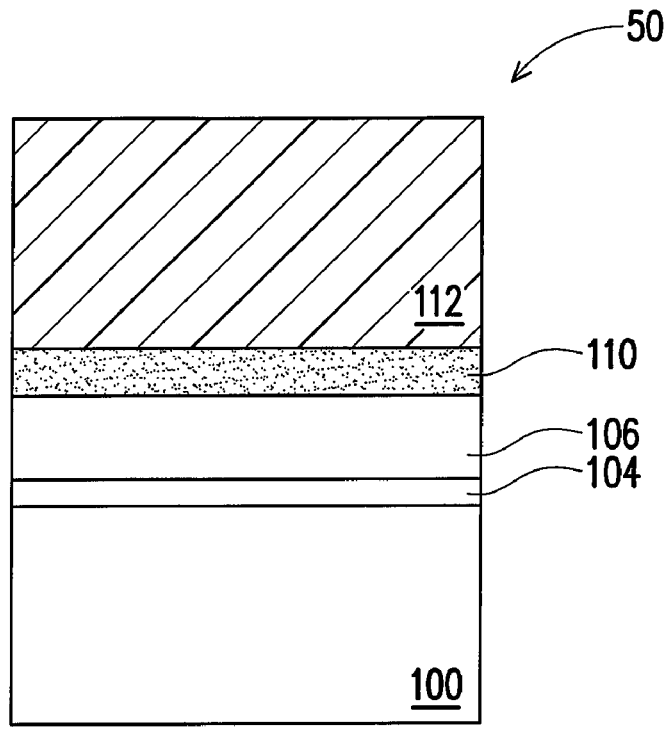

If the to-be-measured device 24 includes the wafer 10 comprising only the to-be-measured pattern 22, the mid layer 20, the pre-layer 16 and a bottom layer 14, and prior to performing the detection, for example, before or after the formation of the to-be-measured material layer 12, the pre-layer 16 has been subjected to a surface treatment, for example, an ion implantation process to form a treatment layer 18 on the surface of the pre-layer 16, and subjected to a subsequent process, such as a thermal process to dematerize the treatment layer 18 and to restore the treatment layer 18 back to the pre-layer 16 or a film similar to the pre-layer 16, the module established with the stacked layer 50 as shown in FIG. 5, and not the module established with the stacked layer 60 as shown in FIG. 6 is selected. The values of the optical parameters of the to-be-measured material layer 112, the mid-material layer 110, the pre-material layer 106, and the wafer material layer 100 in the stacked layer 50 are respectively similar to those of the to-be-measured pattern 22, the mid layer 18, the surface-treated and the subsequent-process-treated pre-layer 16, the bottom layer 14 and the wafer 10 of the to-be-measured device 24.

In one embodiment, the pre-layer 16 of the to-be-measured device 24 is polysilicon, the surface treatment process is an ion implantation process for doping the pre-layer 16 and a doped polysilicon layer 18 is formed on the surface of the pre-layer 16. Then, the module being selected has the stacked layer that includes the pre-material layer 18 being a doped polysilicon material layer and the treatment material layer 108 being a doped amorphous silicon material layer. However, if after the to-be-measured device is surface-treated, and a subsequent process being performed is a thermal process, it is necessary to consider whether the doped amorphous silicon layer 18 is completely crystallized as a doped polysilicon layer. If the doped amorphous silicon layer 18 is completely crystallized as doped polysilicon, a doped amorphous silicon layer (treatment layer) 18 is precluded form the to-be-measured device, and the stacked layer in the selected module should not include a doped amorphous material layer (treatment material layer) 108.

In another embodiment, the pre-layer 16 in the to-be-measured device 24 is polysilicon; the surface treatment process is a nitridation process or an oxidation process to form a silicon oxide layer or a silicon nitride layer 18 on the surface of the pre-layer 16; the pre-layer 16 maintains as a polysilicon layer. Then, the selected module being selected has the stacked layer that includes the pre-material layer 106 being a polysilicon material layer and the treatment material layer being a silicon nitride material layer. Even a thermal process is performed subsequent to the nitridation process or the oxidation process, the thermal process will not affect the silicon nitride or silicon oxide layer 18. Hence, the influence of the thermal process can be disregarded, and the above module is selected.

In another embodiment, the pre-layer 16 in the to-be-measured device 24 is metal, the surface treatment process is an alloying process to from a metal-silicon alloy layer 18 on the surface of the pre-layer 16 and the pre-layer 16 maintains as a metal layer. Then, the selected module includes the stacked layer having the pre-material layer 106 being a metal material layer and the treatment material layer being a metal-silicon alloy material layer. Even a thermal process is performed subsequent to the alloying process, the thermal process will not induce changes to the metal-silicon alloy layer 18. Hence, the influence of the thermal process can be disregarded, and the above module is selected.

Further, after the pre-layer 16 of the to-be-measured device 24 is subjected to a surface treatment process, and according to the type of surface treatment, the treatment layer 18 can be a single layer, a double layer or a multi layer. For example, the pre-layer 16 is polysilicon and subsequent to an ion implantation process, the characteristics, such as the degree of crystallization, the index of refraction or extinction coefficient (K), of the resulting amorphous silicon layer vary along the depth of the layer, which is essentially dividing the resulting amorphous silicon layer into two sub-layers, wherein one sub-layer is an amorphous silicon layer having a higher degree of crystallization, or having a first refraction index or extinction coefficient (K), while the other sub-layer is an amorphous silicon layer having a lower degree of crystallization, or having a second refraction index or extinction coefficient (K). Accordingly, the modules in the library can be modified correspondingly, for example, the treatment layer 108 in the stacked layer 40, 60 as shown in FIGS. 4, 6 may be a single layer, a double layer or a multi layer of amorphous silicon layer having various degrees of crystallization, or having different refraction indices or extinction coefficient (K). On the other hand, the position of the treatment material layer 108 is not limited to being above the pre-material layer 106, the treatment material layer 108 may also be in a mid-section of the treatment material layer 108 or under the treatment material layer if the surface treatment process of the to-be-measured device 24 changes to a mid-section treatment process or a bottom treatment process.

Referring to FIG. 2, after a module has been selected, process step 204 is conducted, in which a correlation process is performed according to the selected module to generate a theoretical curve that actually correlates with the real curve, and to obtain a plurality of parameters corresponding to the theoretical curve. Hence, the relevant information regarding the to-be-measured pattern 112 of the to-be-measured device 10 are acquired. The relevant information regarding the to-be-measured pattern 112 obtained according to the optical critical dimension measuring method of the present invention includes, for example, the top critical dimension (TCD), the middle critical dimension (MCD), the bottom critical dimension (BCD) and the side wall angle (θ). In other embodiments, as the stacked layer of the selected module includes a treatment material layer 108, the optical parameters of each layer in the to-be-detected device 10, such as the refraction index (n) or extinction coefficient (K), or the thickness of the pre-layer 106 is set at a fixed value, and since the thickness of the treatment material layer is difficult to define by the surface treatment step, the thickness of the treatment material layer is set floating during the correlation process to obtain a theoretical curve that is better correlate with the real curve.

Figure 7:
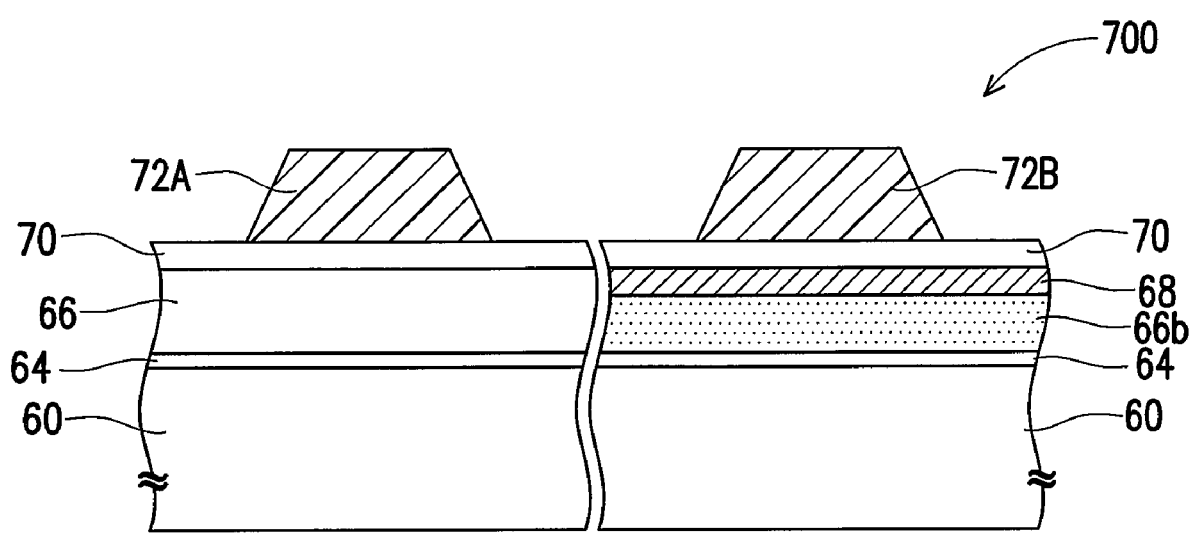
FIG. 7 is a schematic, cross-sectional diagram of a device having two to-be-measured patterns according to another embodiment of the invention.

FIG. 7 is a schematic, cross-sectional diagram illustrating a to-be-measured device having two to-be-measured patterns according to another embodiment of the present invention.

Referring to FIG. 7, in one embodiment, the to-be-measured device 700 is positioned on a silicon wafer 60, which includes a first to-be-measured pattern 72A and a second to-be-measured pattern 72B. The material of the first to-be-measured pattern 72A and a second to-be-measured pattern 72B is, for example, photoresist. A hard mask layer 70 and a gate oxide layer 64 are configured under the first to-be-measured pattern 72A and a second to-be-measured pattern 72B. The material of the hard mask layer includes but not limited to silicon nitride, silicon oxide, silicon oxynitride, silicon carbon nitride, silicon carbon oxide. Polysilicon layers 66, 66b are respectively configured under the first to-be-measured pattern 72A and a second to-be-measured pattern 72B. However, the polysilicon layer under the first to-be-measured pattern 72A is an undoped polysilicon layer 66, while the polysilicon layer under the second to-be-measured pattern 72B has been subjected to a dopant implantation process to form the doped polysilicon layer 66b and a portion of the surface of the doped polysilicon layer 66b is crystallized to form a doped amorphous silicon layer 68. The dopant implantation process is, for example, an N-type dopant implantation process or a P-type dopant implantation process.

During the optical critical dimension detection, the spectrum of the to-be-measured device 700, which correspond to the first real curve of the first to-be-measured pattern 72A and the second real curve of the second to-be-measured pattern 72B, is first obtained.

Thereafter, different modules are selected from the library depending on whether the polysilicon layer of the to-be-measured device 700 has been subjected to an ion implantation process.

If the polysilicon layer of the to-be-measured device 700 has not been subjected to an ion implantation process, the other polysilicon is an undoped polysilicon, and amorphous silicon has not formed on the surface of the polysilicon, the first module is selected from the library. The first module is established with a first stacked layer, and the stacking of each layer in the first stacked layer is as shown in FIG. 5. The to-be-measured material layer 112, the mid-material layer 110, the pre-material layer 106, the bottom material layer 104 and the wafer material layer 100 of the first stacked layer respectively include a photoresist material layer, a mask material layer, an undoped polysilicon material layer, a silicon oxide material layer and a silicon wafer material layer, but not include an amorphous silicon material layer.

If the polysilicon layer of the to-be-measured device 700 has been subjected to an ion implantation process, the other polysilicon is a doped polysilicon, and amorphous silicon is formed on the surface of the polysilicon, the second module is selected from the library. The second module is established with a second stacked layer, and the stacking of each layer in the second stacked layer is as shown in FIG. 6. The to-be-measured material layer 112, the mid-material layer 110, the treatment material layer 110, the pre-material layer 106, the bottom material layer 104 and the wafer material layer 100 of the second stacked layer respectively include a photoresist material layer, a mask material layer, a doped amorphous silicon material layer, a doped polysilicon material layer, a silicon oxide material layer and a silicon wafer layer. The dopants in the doped polysilicon material layer (pre-material layer 106) and the doped amorphous silicon material layer (treatment material layer 108) are the same type as the dopants in the doped polysilicon layer 66b and doped amorphous silicon layer 68 underneath the second to-be-measured pattern 72B. When the dopants of the doped polysilicon layer 66b of the to-be-measured pattern of the to-be-measured device 700 are N-type, the pre-material layer 106 in the stacked layer 60 shown in FIG. 6 is an N-type doped amorphous silicon material layer, and the treatment material layer 108 is an N-type doped amorphous silicon material layer. When the dopants of the doped polysilicon layer 66b in the to-be-measured device 700 are P-type, the pre-material layer 106 in the stacked layer 60 as shown in FIG. 6 is a P-type doped polysilicon material layer. The treatment material layer 108 is a P-type doped amorphous silicon material layer.

In selecting the modules in the library, asides from considering whether the polysilicon layer of the to-be-measured device has been subjected to an ion implantation process, whether a thermal process has been performed on the to-be-measured device 700 and the effects of the thermal process on amorphous silicon layer must also be considered in order to select the appropriate module. If the undoped polysilicon layer underneath the to-be-measured pattern 72A in the to-be-measured device 700 has been subjected to a subsequent thermal process treatment and the undoped polysilicon layer remains unchanged, the first module in the library is selected. However, if the undoped amorphous silicon layer underneath the to-be-measured device 72B in the to-be-measured device 700 has been subjected to a subsequent thermal process treatment, for example, a direct annealing process or an indirect annealing process, which may re-crystallize the undoped amorphous silicon layer to a doped polysilicon layer, and the thermal process is insufficient to cause the doped amorphous layer 68 under the to-be-measured pattern to completely crystallize into a doped polysilicon layer, the second module that includes the doped amorphous silicon layer (treatment material layer) 108 is still being selected from the library. If the subsequent thermal process treatment is sufficient to induce the doped amorphous layer 68 under the to-be-measured pattern to be completely crystallized into a doped polysilicon layer, the third module is selected from the library. The third module is established with a third stacked layer, and the stacking of the third stacked layer is as shown in FIG. 5, wherein the material of each layer is similar to that of the first stacked layer, except the pre-material layer 106 is a doped polysilicon material layer.

After selecting an appropriate module in the library, the selected first module and the selected second module respectively correlate with the first real curve and the second real curve to generate a first theoretical curve that correlates with the first real curve and a second theoretical curve that correlates with the second real curve. A plurality of first parameters that correspond to the first theoretical curve and a plurality of second parameters that correspond to the second theoretical curve are thereby obtained. Hence, the relevant information regarding the to-be-measured pattern 72A and 72B of the to-be-measured device 700, such as the top critical dimension, the middle critical dimension, the bottom critical dimension and the sidewall angle, are resulted. In one embodiment, when the selected second module includes a doped amorphous silicon material layer (treatment material layer 110), during the correlation process, the optical parameters, such as refraction index (n), extinction coefficient (k) of each layer in the stacked layer of the selected module and the thickness of the doped polysilicon material layer (pre-material layer 106) is set at a fixed value, while the thickness of the doped amorphous silicon material layer (treatment material layer 110) is set at floating in order for the theoretical curve to better correlate with the real curve, and more accurate relevant information of the to-be-measured pattern of the to-be-measured device is obtained.

In the optical critical dimension measuring method of the present invention, the modules being constructed in the library take into the considerations of the effects resulted of the treatment process on the to-be-measured device and the subsequent process on the pre-layer under the to-be-measured device. Hence, the theoretical curve correlates better with the real curve. Moreover, during the correlation process, the thickness of the pre-material layer under the to-be-measured pattern is set at a fixed value, while the thickness of the treatment material layer is set at floating to better enhance the correlation between the theoretical curve and the real curve and to obtain a more accurate relevant information of the to-be-measured pattern of the to-be-measured device.

The present invention has been disclosed above in the preferred embodiments, but is not limited to those. It is known to persons skilled in the art that some modifications and innovations may be made without departing from the spirit and scope of the present invention. Therefore, the scope of the present invention should be defined by the following claims.

What is claimed is:

1. A method for measuring optical critical dimension, adapted for measuring a to-be-measured pattern of a to-be-measured device, wherein the to-be-measured pattern comprises a polysilicon layer thereunder, the method comprising:
   obtaining a real curve corresponding to the to-be-measured device;
   selecting a different module in accordance to whether the polysilicon layer has been subjected to an ion implantation process;
      when the polysilicon layer has not been subjected to the ion implantation process, a first module is selected, and the first module is established with a first stacked layer, and the first stacked layer includes a polysilicon material layer but does include an amorphous silicon material layer, and
      when the polysilicon layer has been subjected to the ion implantation process, and a surface of the polysilicon layer is amorphorized into an amorphous silicon layer, then the module being selected is in accordance to whether a thermal process has been performed to sufficiently crystallize the amorphous silicon layer,
      when the polysilicon layer has not been subjected to the thermal process or the amorphous silicon layer has not crystallized completely into the polysilicon layer, a second module is selected, wherein the second module is established with a second stacked layer, and the stacked layer includes a polysilicon material layer and an amorphous silicon material layer above the polysilicon material layer, and
      when the polysilicon layer has been subjected to the thermal process to completely crystallize the amorphous silicon layer into the polysilicon layer, a third module is selected, wherein the third module is constructed with a third stacked layer, wherein the third stacked layer includes a polysilicon material layer, but does not include an amorphous silicon material layer; and
   performing a correlation process based on the selected module to generate a theoretical curve that correlates with the real curve to obtain a plurality of parameters corresponding to the theoretical curve.

2. The method of claim 1, wherein when the second module is selected, a thickness of the polysilicon material layer and optical parameters of the polysilicon material layer and the amorphous silicon layer are set at fixed value, and a thickness of the amorphous silicon material layer is set floating when the correlation process is performed.

3. The method of claim 1, wherein the amorphous silicon material layer in the second stacked layer is a single layer, a double layer or a multi layer.

4. The method of claim 1, wherein the ion implantation process is a doping process, the polysilicon material layer in the first stacked layer is an undoped polysilicon layer, the polysilicon material layer in the stacked layer is a doped polysilicon material layer, and the polysilicon layer in the third stacked layer is a doped polysilicon material layer.

5. The method of claim 4, wherein the doping process is an N-type dopant implantation process or a P-type dopant implantation process.

6. The method of claim 1, wherein when the to-be-measured pattern is a photoresist pattern, and the polysilicon layer further comprises a bottom layer thereunder, the first stacked layer comprises, from a bottom to a top, a first bottom material layer, the polysilicon material layer and a first photoresist material layer, and the second stacked layer comprises, form a bottom to a top, a second bottom material layer, a polysilicon material layer, the amorphous silicon material layer and a second photoresist material layer.

7. The method of claim 1, wherein when the to-be-measured pattern is a photoresist pattern, and the polysilicon layer and the to-be-measured pattern further comprise a mid layer there-between, the first stacked layer comprises, from a bottom to a top, a polysilicon material layer, a first mid-material layer and a first photoresist material layer, and the second stacked layer comprises, from a bottom to a top, the polysilicon material layer, the amorphous material layer, a second mid-material layer and a second photoresist material layer.

8. The method of claim 1, wherein the thermal process comprises a direct anneal process or an indirect anneal process.

9. The method of claim 1, wherein the optical critical dimension method includes a normal incident (NI) optical critical dimension measuring method or a spectroscopic ellipsometry (SE) optical critical dimension (SE-OCD) measuring method, wherein the spectroscopic ellipsometry optical critical dimension measuring method includes a spectrum critical dimension measuring method.

10. A method of establishing n optical critical dimension module, wherein the optical critical dimension module is applicable in measuring a to-be-measured pattern of a to-be-measured device, the to-be-measured pattern comprises a pre-layer, the method comprising:
   establishing a plurality of modules according to the to-be-measured pattern, a type of each layer underneath the to-be-measured pattern and a process being performed on the each layer, and the modules comprising:
      a first module, applicable when the pre-layer of the to-be-measured device has not been subjected to a treatment process, the first module is constructed with a first stacked layer, and the first stacked layer includes, from a bottom to a top, a first pre-material layer and a first to-be-measured material layer, but does not include a treatment layer; and
      a second module, applicable when the pre-layer of the to-be-measured device has been subjected to the treatment process to form a treatment layer, the second module is constructed with a second stacked layer, and the second stacked layer includes a second pre-material layer, a treatment material layer and a second to-be-measured material layer.

11. The method of claim 10, wherein the treatment material layer in the second stacked is a single layer, a double layer or a multi layer.

12. The method of claim 10, wherein the pre-layer comprises a polysilicon layer, and the pre-material layer comprises a polysilicon material layer, the treatment process comprises a dopant implantation process, an oxidation process or a nitridation process, the treatment material layer comprises a doped amorphous silicon layer, an oxide layer or a nitride layer, and the treatment material layer comprises a doped amorphous silicon material layer, a silicon oxide material layer or a silicon nitride material layer.

13. The method of claim 10, wherein the modules further comprises a third module, and the third module is established with a third stacked layer and the third stacked layer comprises, from a bottom to a top, a doped polysilicon material layer and a to-be-measured material layer, and the doped polysilicon material layer and the to-be-measured material does not include a doped amorphous silicon layer therebetween, wherein the third module is applied to the to-be-measured device when subsequent to the treatment process being a dopant implantation process, a thermal process is performed to crystallize the amorphous silicon layer into a doped polysilicon layer.

14. The method of claim 10, wherein the pre-layer comprises a metal layer, the pre-material layer comprises a metal material layer, the treatment layer comprises a metal-silicon alloy layer, the treatment material layer comprises a metal-silicon alloy material layer.

15. The method of claim 10, wherein the pre-layer and the to-be-measured pattern further comprises a mid layer, the first stacked layer further comprises a mid-material layer positioned between the pre-material layer and the to-be-measured material layer, the second stacked layer further comprises a mid-material layer positioned between the treatment material layer and the to-be-measured material layer.

16. The method of claim 10, wherein when the pre-layer further comprises a bottom layer there-under, the first stacked layer further comprises a first bottom material layer under the pre-material layer, the second stacked layer further comprises a second bottom material layer under the pre-material layer.

17. The method of claim 10, wherein the optical critical dimension method includes a normal incident (NI) optical critical dimension measuring method or a spectroscopic ellipsometry (SE) optical critical dimension (SE-OCD) measuring method, wherein the spectroscopic ellipsometry optical critical dimension measuring method includes a spectrum critical dimension measuring method.

18. An optical critical dimension measuring method, applicable in measuring a first to-be-measured pattern and a second to-be-measured pattern, wherein the first to-be-measured pattern comprises an undoped polysilicon layer underneath, and the second to-be-measured pattern comprises a doped polysilicon layer underneath, and a part of the doped polysilicon layer is amorphorized into a doped amorphous silicon layer, the method comprising:
obtaining a first real curve that corresponds to the first to-be-measured pattern and a second real curve that corresponds to the second to-be-measured pattern; and
selecting a first module and a second module, which is different from the first module, and performing a correlation process correspondingly with the first real curve and the second real curve to generate a first theoretical curve that correlates with the first real curve and a second theoretical curve that correlates with the second real curve to obtain a plurality of first parameters corresponding to the first theoretical curve and a plurality of parameters corresponding to the second theoretical curve.

19. The method of claim 18, wherein
the first module is established with a first stacked layer, and the first stacked layer comprises an undoped polysilicon material layer, but does not comprise a amorphous silicon material layer; and
the second module is established with a second stacked layer, and the second stacked layer comprises a doped polysilicon material layer and a doped amorphous silicon material layer positioned above the doped polysilicon material layer.

20. The method of claim 19, wherein when the second module is selected to correlate with the second real curve, a thickness of the doped polysilicon layer is set at a fixed value, and optical parameters of the doped polysilicon material layer and the doped amorphous silicon material layer and a thickness of the second doped polysilicon material layer are set at floating.

21. The method of claim 19, wherein the optical critical dimension method includes a normal incident (NI) optical critical dimension measuring method or a spectroscopic ellipsometry (SE) optical critical dimension (SE-OCD) measuring method, wherein the spectroscopic ellipsometry optical critical dimension measuring method includes a spectrum critical dimension measuring method.

22. A method for measuring optical critical dimension, adapted for measuring a to-be-measured pattern of a to-be-measured device, wherein the to-be-measured pattern comprises a polysilicon layer thereunder, the method comprising:
obtaining a real curve corresponding to the to-be-measured device;
selecting a different module in accordance to whether the polysilicon layer has been subjected to an ion implantation process; and
performing a correlation process based on the selected module to generate a theoretical curve that correlates with the real curve to obtain a plurality of parameters corresponding to the theoretical curve.

23. The method of claim 22, further comprising selecting a first module when the polysilicon layer has not been subjected to the ion implantation process, wherein the first module is established with a first stacked layer including a polysilicon material layer but does not include an amorphous silicon material layer.

24. The method of claim 22, wherein a surface of the polysilicon layer is amorphorized into an amorphous silicon layer when the polysilicon layer has been subjected to the ion implantation process, then the module being selected is in accordance to whether a thermal process has been performed to sufficiently crystallized the amorphous silicon layer.

25. The method of claim 24, further comprising selecting a second module when the polysilicon layer has not been subjected to a thermal process or the amorphous silicon layer has not crystallized completely into the polysilicon layer, wherein the second module is established with a second stacked layer including a polysilicon material layer and an amorphous silicon material layer above the polysilicon material layer.

26. The method of claim 24, further comprising selecting a third module when the polysilicon layer has been subjected to the thermal process to completely crystallize the amorphous silicon layer into the polysilicon layer, wherein the third module is constructed with a third stacked layer including a polysilicon material layer but does not include an amorphous silicon material layer.

27. the method of claim 25, wherein when the second module is selected, a thickness of the polysilicon material layer and optical parameters of the polysilicon material layer and the amorphous silicon layer are set at a fixed value, and a thickness of the amorphous silicon material layer is set floating when the correlation process is performed.

28. The method of claim 25, wherein the amorphous silicon material layer in the second stacked layer is a single layer, a double layer or a multi layer.

29. The method of claim 23, wherein the polysilicon material layer in the first stacked layer is an undoped polysilicon layer.

30. The method of claim 25, wherein the polysilicon material layer in the second stacked layer is a doped polysilicon material layer.

31. The method of claim 26, wherein the polysilicon layer in the third stacked layer is a doped polysilicon material layer.

32. The method of claim 23, wherein when the to-be-measured pattern is a photoresist pattern and the polysilicon layer further comprises a bottom layer thereunder, the first stacked layer comprises, from a bottom to a top, a first bottom material layer, the polysilicon material layer and a first photoresist material layer.

33. The method of claim 25, wherein when the to-be-measured pattern is a photoresist pattern and the polysilicon layer further comprises a bottom layer thereunder, the second stacked layer comprises, form a bottom to a top, a second bottom material layer, a polysilicon material layer, the amorphous silicon material layer and a second photoresist material layer.

34. The method of claim 23, wherein when the to-be-measured pattern is a photoresist pattern, and the polysilicon layer and the to-be-measured pattern further comprise a mid layer there-between, the first stacked layer comprises, from a bottom to a top, a polysilicon material layer, a first mid-material layer and a first photoresist material layer.

35. The method of claim 25, wherein when the to-be-measured pattern is a photoresist pattern, and the polysilicon layer and the to-be-measured pattern further comprise a mid layer there-between, the second stacked layer comprises, from a bottom to a top, the polysilicon material layer, the amorphous material layer, a second mid-material layer and a second photoresist material layer.

36. The method of claim 24, wherein the thermal process comprises a direct anneal process or an indirect anneal process.

37. The method of claim 22, wherein the optical critical dimension method includes a normal incident (NI) optical critical dimension measuring method or a spectroscopic ellipsometry (SE) optical critical dimension (SE-OCD) measuring method, wherein the spectroscopic ellipsometry optical critical dimension measuring method includes a spectrum critical dimension measuring method.

* * * * *